United States Patent
Foguet et al.

(10) Patent No.: US 7,205,405 B2
(45) Date of Patent: Apr. 17, 2007

(54) PROCESS FOR PREPARING 3-(2-(4-(6-FLUOROBENZO(D)ISOXAZOL-3-YL)-PIPERIDIN-1-YL)-ETHYL)-2-METHYL-6,7,8,9-TETRAHYDRO-4H-PYRIDO-(1,2-A)PYRIMIDIN-4-ONE

(75) Inventors: Rafael Foguet, Barcelona (ES); Jorge Ramentol, Barcelona (ES); Diego Fernandez-Cano, Barcelona (ES); Miguel P. Armengol, Barcelona (ES); Francesc X. Camps, Barcelona (ES); Juan Sallares, San Cugat (ES); Inés Petschen, Barcelona (ES); Mireia Pasto, Barcelona (ES); Esther Gordo, Barcelona (ES)

(73) Assignee: Ferrer Internacional, S.A., Barcelona (ES)

( * ) Notice: Subject to any disclaimer, the term of this patent is extended or adjusted under 35 U.S.C. 154(b) by 206 days.

(21) Appl. No.: 10/503,478

(22) PCT Filed: Mar. 3, 2003

(86) PCT No.: PCT/EP03/02157

§ 371 (c)(1),
(2), (4) Date: Sep. 28, 2004

(87) PCT Pub. No.: WO03/074522

PCT Pub. Date: Sep. 12, 2003

(65) Prior Publication Data

US 2005/0143395 A1 Jun. 30, 2005

(30) Foreign Application Priority Data

Mar. 5, 2002 (ES) .............................. 200200531

(51) Int. Cl.
*C07D 239/70* (2006.01)
*C07D 261/20* (2006.01)

(52) U.S. Cl. ..................................... 544/282; 546/198

(58) Field of Classification Search ................ 544/282; 546/198

See application file for complete search history.

(56) References Cited

FOREIGN PATENT DOCUMENTS

| EP | 0 196 132 A | 10/1986 |
|---|---|---|
| EP | 0 368 388 A | 5/1990 |
| EP | 0 453 042 A | 10/1991 |
| WO | WO-01 85731 A | 11/2001 |

OTHER PUBLICATIONS

Kim, et al., "An Efficient Synthesis of Risperidone via Stille Reaction: Antipsychotic, 5HT2, and Dopamine-D2-Antagonist," Arch. Pharm. Res., vol. 28, No. 9, 1019-1022, 2005.*

* cited by examiner

*Primary Examiner*—Deepak Rao
*Assistant Examiner*—Cecilia Jaisle
(74) *Attorney, Agent, or Firm*—Birch, Stewart, Kolasch & Birch, LLP

(57) ABSTRACT

The process consists in condensing (2-methyl-6,7,8,9-tetrahydro-4 H-pyrido-[1,2-a]pyrimidin-3-yl)-acetaldehyd with 6-fluoro-3-piperidinyl)-1,2-benzisoxazole to yield the intermediate enamine, 3-{2-[4-(6-fluoro-benzo[d]isoxazol-3-yl)-piperidin-1-yl]vinyl}-2-methyl-6,7,8,9-tetrahydro-pyrido[1,2,-a]pyrimidin-4-one followed by reduction of such an enamine.

9 Claims, No Drawings

PROCESS FOR PREPARING 3-(2-(4-(6-FLUOROBENZO(D)ISOXAZOL-3-YL)-PIPERIDIN-1-YL)-ETHYL)-2-METHYL-6,7,8,9-TETRAHYDRO-4H-PYRIDO-(1,2-A)PYRIMIDIN-4-ONE

CROSS-REFERENCE TO RELATED APPLICATIONS

This application claims the benefit of PCT/EP03/02157, filed Mar. 3, 2003.

FIELD OF THE INVENTION

The present invention relates to a process for preparing 3-{2-[4-(6-fluorobenzo[d]isoxazol-3-yl)-piperidin-1-yl]-ethyl}-2-methyl-6,7,8,9-tetrahydro-4H-pyrido-[1,2-a]pyrimidin-4-one of formula I.

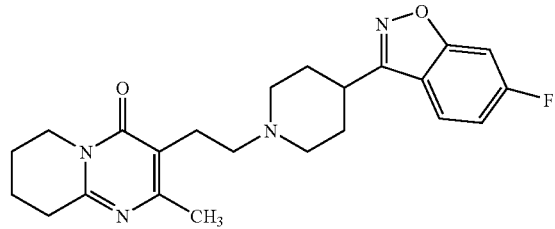

The compound of formula I, known as risperidone, is a pharmaceutically active compound for its antipsychotic properties.

A further embodiment of this invention are the compounds of formula II, (2-methyl-4-oxo-6,7,8,9-tetrahydro-4H-pyrido[1,2-a]pyrimidin-3-yl)-acetaldehyde, and of formula III, 3-{2-[4-(6-fluorobenzo[d]isoxazol-3-yl)-piperidin-1-yl]-vinyl}-2-methyl-6,7,8,9-tetrahydro-pyrido[1,2-a]pyrimidin-4-one. These compounds are synthetic intermediates in the process for preparing the compound of formula I.

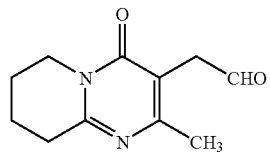

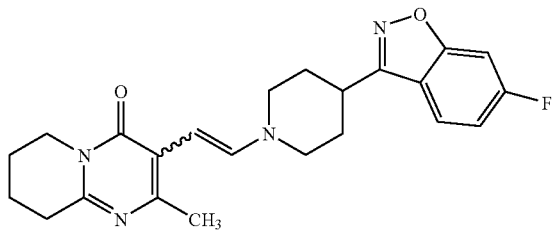

The compounds II and III have not previously been described.

BACKGROUND OF THE INVENTION

EP 0196132 discloses different procedures for the preparation of 3-{2-[4-(6-fluorobenzo[d]isoxazol-3-yl)-piperidin-1-yl]-ethyl}-2-methyl-6,7,8,9-tetrahydro-4H-pyrido-[1,2-a]pyrimidin-4-one (I), which comprise cyclization of different intermediates by intermolecular condensation reaction among different functional groups to provide 2-methyl-6,7,8,9-tetrahydro-4H-pyrido-[1,2-a]pyrimidin-4-one system. Most of these procedures hold in common the use of very complex intermediates and the implementation of problematic reactions in the final synthesis steps that have necessarily an influence on the total cost of the final process.

In EP 0196132, 3-{2-[4-(6-fluorobenzo[d]isoxazol-3-yl)-piperidin-1-yl]-ethyl}-2-methyl-6,7,8,9-tetrahydro-4H-pyrido-[1,2-a]pyrimidin-4-one (I) may also be prepared by another procedure that comprises formation of a C—N bond by intermolecular N-alkylation reaction of 6-fluoro-3-(4-piperidinyl)-benzo[d]isoxazole (IV) with 3-(2-chloroethyl)-2-methyl-6,7,8,9-tetrahydro-4H-pyrido[1,2-a]pyrimidin-4-one or analogous derivatives with other leaving groups (V) (Scheme 1).

Scheme 1

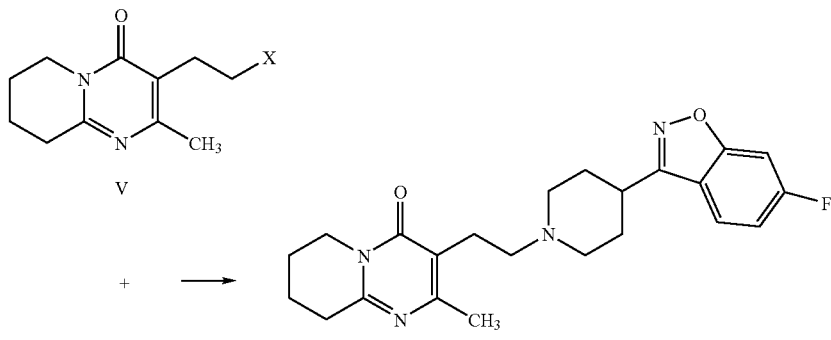

-continued

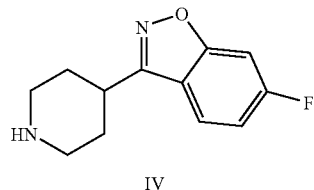

IV

ES2006888, ES2006889 and ES2050069 disclose different procedures for the preparation of 3-{2-[4-(6-fluorobenzo[d]isoxazol-3-yl)-piperidin-1-yl]-ethyl}-2-methyl-6,7,8,9-tetrahydro-4H-pyirido-[1,2-a]pyrimidin-4-one (I), which hold in common a final intramolecular cyclization stage of different types of closely related intermediates to provide the isoxazole ring present in the required product.

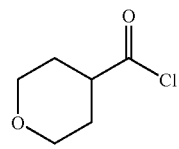

VI

ES2074966 discloses a procedure for the preparation of 3-{2-[4-(6-fluorobenzo[d]isoxazol-3-yl)-piperidin-1-yl]-ethyl}-2-methyl-6,7,8,9-tetrahydro-4H-pyirido-[1,2-a]pyrimidin-4-one (I) based on final cyclization of the piperidine ring by double intermolecular N-alkylation reaction of 3-(2-aminoethyl)-2-methyl-6,7,8,9-tetrahydro-4H-pyrido[1,2-a]pyrimidin-4-one (VII) with a pentane-like derivative containing the benzo[d]isoxazole system and the two leaving groups in positions 1 and 5 of general formula VIII (Scheme 2).

Scheme 2

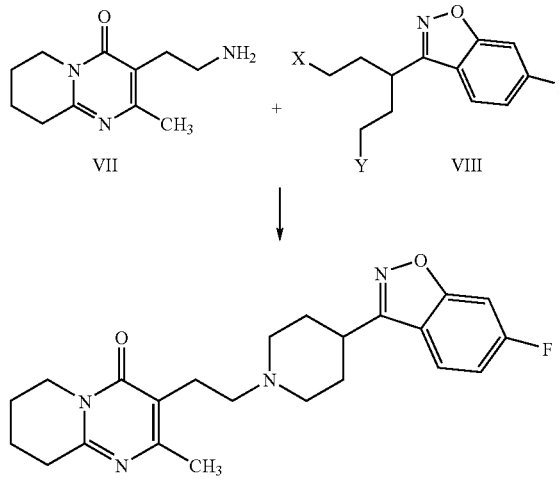

One of the starting materials used in the preparation of intermediate VIII is 4-tetrahydropyrancarbonyl chloride (IX)

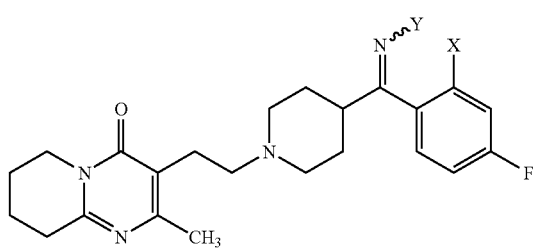

IX which is not commercially available. In addition, the preparation of VIII from IX comprises five steps (ES2074966).

The present invention provides an alternative process for the preparation of 3-{2-[4-(6-fluoro-benzo[d]isoxazol-3-yl)-piperidin-1-yl]-ethyl}-2-methyl-6,7,8,9-tetrahydro-4H-pyrido-[1,2-a]pyrimidin-4-one (I), which is illustrated in Scheme 3:

Scheme 3

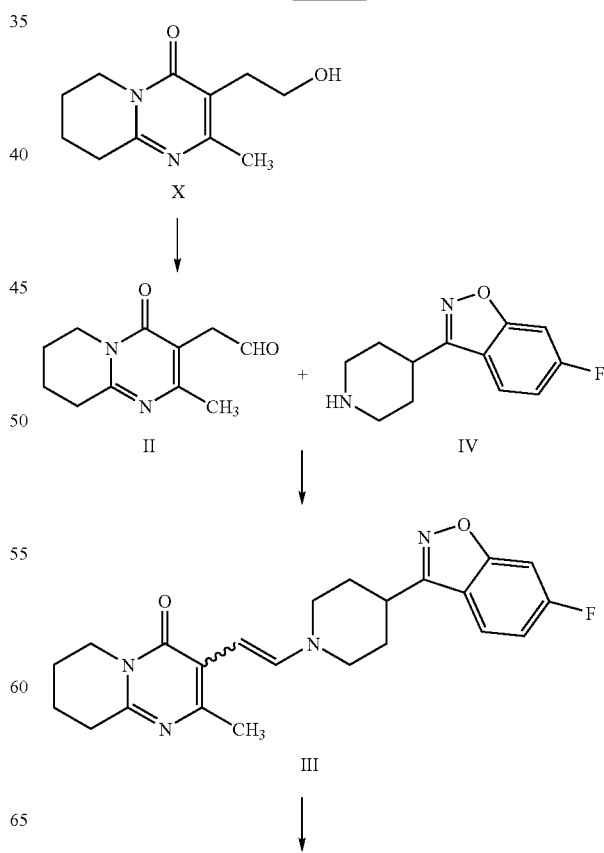

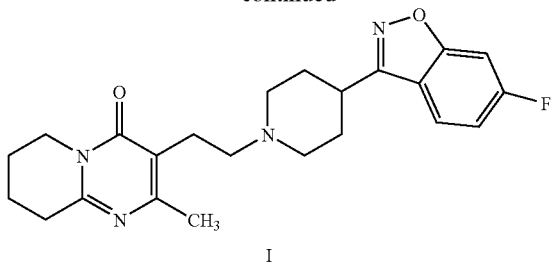

I

The compound of formula II of the present invention, (2-methyl-4-oxo-6,7,8,9-tetrahydro-4H-pyrido[1,2-a]pyrimidin-3-yl)-acetaldehyde is prepared from 3-(2-hydroxyethyl)-2-methyl-6,7,8,9-tetrahydro-4H-pyrido[1,2-a]pyrimidin-4-one (X) (the preparation of this compound is described in H. Fujita et al. *Ann. Rep. Sankyo Res. Lab.* 1977, 29, 75–78).

The enamine of formula III, 3-{2-[4-(6-fluorobenzo[d]isoxazol-3-yl)-piperidin-1-yl]-vinyl}-2-methyl-6,7,8,9-tetrahydro-pyrido[1,2-a]pyrimidin-4-one, is obtained from aldehyde II and by condensation with 6-fluoro-3-(4-piperidinyl)-benzo[d]isoxazole of formula IV (the preparation of compound IV is described in ES8405791).

The applicants found out that the enamine of formula III is easily reducible to 3-{2-[4-(6-fluorobenzo[d]isoxazol-3-yl)-piperidin-1-yl]-ethyl}-2-methyl-6,7,8,9-tetrahydro-4H-pyrido-[1,2-a]pyrimidin-4-one (I) by means of the action of a reducing agent.

Alternatively, the formation of the final product, 3-{2-[4-(6-fluorobenzo[d]isoxazol-3-yl)-piperidin-1-yl]-ethyl}-2-methyl-6,7,8,9-tetrahydro-4H-pyrido-[1,2-a]pyrimidin-4-one (I), may occur directly and advantageously from (2-methyl-4-oxo-6,7,8,9-tetrahydro-4H-pyrido[1,2-a]pyrimidin-3-yl)-acetaldehyde (II) and 6-fluoro-3-(4-piperidinyl)-benzo[d]isoxazole (IV) under reductive amination conditions in a single-stage synthesis process.

The process described in the present invention combines in a unique way elegance in synthesis and compliance with the requirements for cost, safety and ecology in the production of the active substance risperidone (I). The chemical procedure is easily reproducible on a large scale through simple and high-yield synthesis steps which lead to a high-quality final product.

The compounds of formula II and III have not previously described and form part of this invention.

DETAILED DESCRIPTION OF THE INVENTION

For the oxidation of 3-(2-hydroxyethyl)-2-methyl-6,7,8,9-tetrahydro-4H-pyrido[1,2-a]pyrimidin-4-one (X) to provide 2-methyl-4-oxo-6,7,8,9-tetrahydro-4H-pyrido[1,2-a]pyrimidin-3-yl)-acetaldehyde (II), procedures based on the use of dimethyl sulfoxide in the presence of an electrophilic agent, such as dicyclohexylcarbodiimide, acetic anhydride, trifluoroacetic anhydride, sulphur trioxide, or preferably oxalyl chloride are preferred. The reaction is carried out in an inert solvent, preferably methylene chloride, and in the presence of a base, preferably triethylamine, at a temperature ranging from −78° C. to room temperature.

The condensation reaction between (2-methyl-4-oxo-6,7,8,9-tetrahydro-4H-pyrido[1,2-a]pyrimidin-3-yl)-acetaldehyde (II) and 6-fluoro-3-(4-piperidinyl)-1,2-benzisoxazole (IV) or any of its salts, to provide intermediate enamine III, is performed in an inert solvent, preferably toluene, at a temperature ranging from 20° C. to 150° C., preferably at reflux temperature. The reaction may be catalysed by adding acids or bases. The reaction may be favoured by chemical equilibrium displacement through an uptake system of the water released in the reaction, for example the use of molecular sieves, or other desiccants. Preferably the water may be displaced from the reaction medium by azeotropic distillation.

The reduction of intermediate enamine III to provide the final compound I may be carried out using different hydrides, such as sodium hydride, potassium hydride, magnesium hydride, calcium hydride, sodium borohydride, sodium cyanoborohydride, sodium trisacetoxyborohydride, lithium hydride, lithium and alluminium hydride, sodium and aluminium hydride, aluminium hydride, sodium and bis(2-methoxyethoxy) alluminium hydride, alluminium mono($C_{1-4}$ alcoxy)aluminium hydride, lithium di($C_{1-4}$ alcoxy) aluminium hydride, sodium and diethylalluminium hydride or the mixtures thereof, optionally in the presence of a salt, base or inorganic acid. The reduction may also be carried out using a borane or diborane, optionally in the presence of an amine. Preferably, sodium cyanoborohydride or sodium borohydride are used in the presence of acetic acid. The reaction may be performed in different poorly polar solvents, such as tetrahydrofuran (THF), ethyl ether, tert-butylmethylether, mixtures of toluene and THF, and the like, or polar solvents, such as ethanol, methanol, isopropanol, butanol, or other high-boiling point alcohols, such as water, mixtures of ethanol and water, and the like, ethanol being the most convenient. The reaction temperature may range from −20° C. to 80° C., preferably at about 25° C.

The following Examples are intended to illustrate the present invention but not to restrict the scope thereto.

EXAMPLE 1

(2-methyl-4-oxo-6,7,8,9-tetrahydro-4H-pyrido[1,2-a] pyrimidin-3-yl)-acetaldehyde (II)

To a stirred mixture of 2.2 mL (25.22 mmoles) of oxalyl chloride in 70 mL of anhydrous methylene chloride at low temperature (−70° C. to −50° C.) and under inert atmosphere, 4.1 mL (57.78 mmoles) of dimethyl sulfoxide were added. Then, a solution of 5 g (24.02 mmoles) of 3-(2-hydroxyethyl)-2-methyl-6,7,8,9-tetrahydro-4H-pyrido[1,2-a]pyrimidin-4-one (X) in 30 mL of methylene chloride was added. After 30 minutes, 14.6 mL (104.75 mmoles) of triethylamine were added and the mixture was warmed for 45 minutes at room temperature. 75 mL of water were poured and the organic phase was decanted. The aqueous phase was removed with methylene chloride. All the organic phases were dried over anhydrous sodium sulphate, filtered and the solvent was evaporated to give 4.90 g (99%) of (2-methyl-4-oxo-6,7,8,9-tetrahydro-4H-pyrido[1,2-a]pyrimidin-3-yl)-acetaldehyde (II) as an oily residue. The compound thus obtained was pure enough as to be used in the subsequent reaction step with no prior purification.

$^1$HNMR (CDCl$_3$), δ (ppm): 9.71 t, J=1.2 Hz, 1H, aldehyde; 3.93 t, J=6.0 Hz, 2H, C$\underline{H}_2$—N); 3.66 d, J=1.2 Hz, 2H, C$\underline{H}_2$CHO; 2.90 t, J=6.8 Hz, 2H, CH$_2$C$\underline{H}_2$C(N)=N, 2.22 s, 3H, C$\underline{H}_3$; 2.00–1.85 m, 4H, CH$_2$C$\underline{H}_2$C$\underline{H}_2$CH$_2$.

$^{13}$CNMR (CDCl$_3$), δ (ppm): 198.59 $\underline{C}$HO; 162.65 N$\underline{C}$O; 160.69 N—$\underline{C}$=N, 157.49 N—$\underline{C}$=C, 113.25 $\underline{C}$=C—N, 43.22, 41.31, 31.72 3×$\underline{C}$H$_2$; 22.06, 19.36 CH$_2$$\underline{C}$H$_2$$\underline{C}$H$_2$CH$_2$; 21.80 $\underline{C}$H$_3$.

R$_f$ (SiO$_2$/ethyl acetate: methanol, 9:1)=0.2

EXAMPLE 2

3-{2-[4-(6-fluorobenzo[d]isoxazol-3-yl)-piperidin-1-yl]-vinyl}-2-methyl-6,7,8,9-tetrahydro-pyrido[1,2-a]pyrimidin-4-one (III)

A mixture of 2.96 g (14.33 mmoles) of (2-methyl-4-oxo-6,7,8,9-tetrahydro-4H-pyrido[1,2-a]pyrimidin-3-yl)-acetaldehyde (II), 3.16 g (14.33 mmoles) of 6-fluoro-3-(4-piperidinyl)-1,2-benzisoxazole (IV) and 50 mL of toluene was transferred to a Dean Stark apparatus. The mixture was brought to boiling point, refluxed for 3 hours, and the solvent was evaporated under reduced pressure to give 5.70 g (97.3%) of 3-{2-[4-(6-fluorobenzo[d]isoxazol-3-yl)-piperidin-1-yl]-vinyl}-2-methyl-6,7,8,9-tetrahydro-pyrido[1,2-a]pyrimidin-4-one (III) as a deep orange solid. The compound thus obtained was pure enough as to be used in the subsequent reaction step with no prior purification or optionally crystallized from an organic solvent, preferably ethanol.

$^1$H-NMR (CDCl$_3$), δ (ppm): 7.85 d, J=14 Hz, 1H, =CHN; 7.67 dd, J$_1$=8.8 Hz, J$_2$=4.8 Hz, 1H, CH aromatic; 7.25 dd, J$_1$=8.4 Hz, J$_2$=2.0 Hz, 1H, CH aromatic; 7.07 m, 1H, CH aromatic; 5.16 d, J=14 Hz, 1H, CH=CHN; 3.97 t, J=6.4 Hz, 2H, CH$_2$—NCO; 3.65 d, J=12.8 Hz, 2H, 3.23 m, 1H, 2.95 m, 2H, 2.88 t, J=6.6 Hz, 2H, CH$_2$C=N(N); 2.34 s, 3H, CH$_3$; 2.11 m, 4H; 1.97 m, 2H, 1.88 m, 2H.

$^{13}$C-NMR (CDCl$_3$), δ (ppm): 165.32–162.83, d, J$_{C-F}$=249 Hz, C aromatic; 163.92–163.79, d J$_{C-F}$=13 Hz, C aromatic; 162.83 C aromatic; 160.98 C aromatic; 160.64 C aromatic; 152.60 C aromatic; 143.59 CH enamine; 122.40–122.29 d J$_{C-F}$=11 Hz, CH aromatic; 118.42 C aromatic; 117.13–117.1 d J$_{C-F}$=2 Hz, C aromatic; 112.53–112.28 d, J$_{C-F}$=25 Hz, CH aromatic; 97.58–97.31 d, J$_{C-F}$=27 Hz, CH aromatic; 91.87 CH enamine; 48.16 CH$_2$; 42.55 CH$_2$; 34.43 CH; 31.29 CH$_2$; 29.69 CH$_2$; 22.19 CH$_2$; 22.07 CH$_3$; 19.38 CH$_2$;

R$_f$ (SiO$_2$/ethyl:methanol acetate, 9:1)=0.21
R$_f$ (SiO$_2$/chloroform:methanol, 9:1)=0.50

EXAMPLE 3

3-{2-[4-(6-fluorobenzo[d]isoxazol-3-yl)-piperidin-1-yl]-ethyl}-2-methyl-6,7,8,9-tetrahydro-4H-pyrido[1,2-a]pyrimidin-4-one (I)

To a suspension of 1.39 g (3,42 mmoles) of 3-{2-[4-(6-fluorobenzo[d]isoxazol-3-yl)-piperidin-1-yl]-vinyl}-2-methyl-6,7,8,9-tetrahydro-pyrido[1,2-a]pyrimidin-4-one (III) in 22 mL of absolute ethanol and 1 mL of glacial acetic acid under stirring at room temperature and in a protective atmosphere, 0.254 g (4.04 mmoles) of sodium cyanoborohydride in small portions was added for 1 hour. After 1.5 hour, the solvent was evaporated and the crude product obtained was dissolved in 250 mL of ethyl acetate. The organic phase was successively washed with 50 mL of 1M aqueous sodium bicarbonate solution, 50 mL of water and 50 mL of saturated sodium chloride solution and dried over anhydrous magnesium sulphate. The resultant solution was filtered and the solvent was evaporated to yield 1.17 g of a residual solid (83%), which was diluted in methylene chloride and purified by column chromatography (silica gel). Elution of the column was with methylene chloride, methanol and triethylamine (95:5:1). The pure fractions were collected and the solvent was evaporated under reduced pressure to give 0.83 g (70.9%) of 3-{2-[4-(6-fluorobenzo[d]isoxazol-3-yl)-piperidin-1-yl]-ethyl}-2-methyl-6,7,8,9-tetrahydro-4H-pyrido-[1,2-a]pyrimidin-4-one (I). Optionally, the reaction crude product was purified by crystallization from a suitable organic solvent, preferably ethanol or 4-methyl-2-pentanone.

$^1$H-NMR (CDCl$_3$), δ (ppm): 7.71 dd, J$_1$=8.8 Hz, J$_2$=5.2 Hz, 1H, CH aromatic; 7.23 dd, J$_1$=8.6 Hz, J$_2$=2.2 Hz, 1H, CH aromatic; 7.05 ddd, J$_1$=8.8 Hz, J$_2$=8.6 Hz, J$_3$=2.2 Hz, 1H, CH aromatic; 3.93 t, J=6.2 Hz, 2H, CH$_2$; 3.18 t, J=11.6 Hz, 2H, CH$_2$; 3.08 m, 1H, CH; 2.87 t, J=6.6 Hz, 2H, CH$_2$; 2.77 m, 2H, CH$_2$; 2.55 m, 2H, CH$_2$; 2.31 s, 3H, CH$_3$; 2.27 m, 2H, CH$_2$; 2.09 m, 4H, 2×CH$_2$; 1.96 m, 2H, CH$_2$; 1.89 m, 2H, CH$_2$.

$^{13}$C-NMR (CDCl$_3$), δ (ppm): 165.26–166,77, d, J$_{C-F}$=249 Hz, C aromatic; 163.88–163.75, d, J$_{C-F}$=14 Hz, C aromatic; 162.56; 161.09 C aromatic; 158.39 C aromatic; 155.87 C aromatic; 122.67–122.55 d, J$_{C-F}$=11 Hz, CH aromatic; 119.27 C aromatic; 117.28 C aromatic; 112.35–112.10 d, J$_{C-F}$=25 Hz, CH aromatic; 97.48–97.21 d, J$_{C-F}$=27 Hz, CH aromatic; 56.68 CH$_2$; 53.35 CH$_2$; 42.66 CH$_2$; 34.59 CH; 31.41 CH$_2$; 30.53 CH$_2$; 23.74 CH$_2$; 21.95 CH$_2$; 21.24 CH$_3$; 19.20 CH$_2$.

The invention claimed is:

1. A process for the preparation of 3-{2-[4-(6-fluorobenzo[d]isoxazol-3-yl)-piperidin-1-yl]-ethyl}-2-methyl-6,7,8,9-tetrahydro-4H-pyrido-[1,2-a]pyrimidin-4-one of formula I:

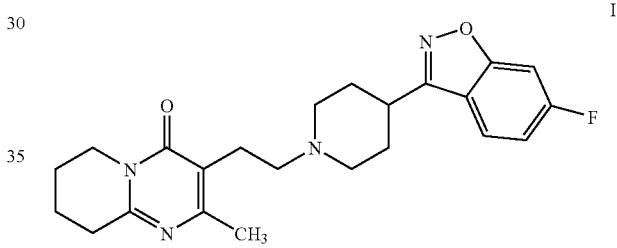

which comprises condensation of (2-methyl-4-oxo-6,7,8,9-tetrahydro-4H-pyrido[1,2-a]pyrimidin-3-yl)-acetaldehyde of formula II:

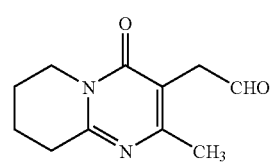

with 6-fluoro-3-(4-piperidinyl)-1,2-benzisoxazole of formula IV:

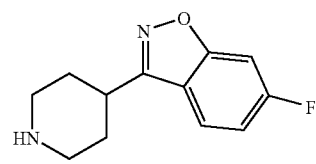

or any of its salts to provide the intermediate enamine 3-{2-[4-(6-fluorobenzo[d]isoxazol-3-yl)-piperidin-1-yl]-vinyl}-2-methyl-6,7,8,9-tetrahydro-pyrido[1,2-a] pyrimidin-4-one of formula III:

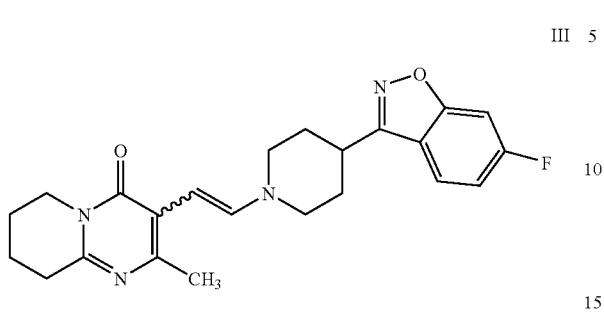

followed by reduction of same in the presence of a hydride, optionally in the presence of a salt, acid or inorganic base, and in the presence of a suitable inert solvent, the reactions being performed by either isolating intermediate III or in a single stage synthesis without isolating intermediate III.

2. A process according to claim 1, wherein the reduction of the reacting itermediate enamine of formula III is carried out with a hydride or borane in a suitable solvent.

3. A process according to claim 2, wherein the hydride is sodium cyanoborohydride or sodium borohydride, optionally accompanied by acetic acid.

4. A process according to claim 2, wherein the suitable solvent is ethanol.

5. An enamine of formula III:

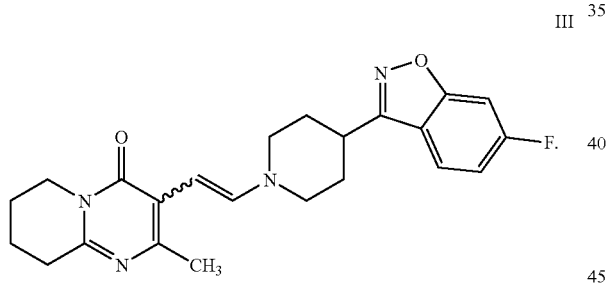

6. An aldehyde of formula II:

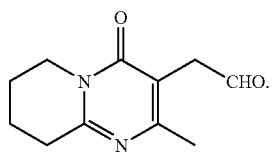

7. A process for the preparation of the compound of formula II:

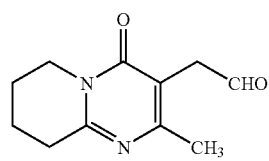

which comprises oxidation of 3-(2-hydroxyethyl)-2-methyl-6,7,8,9-tetrahydro-4H-pyrido [1,2-a]pyrimidin-4-one of formula X:

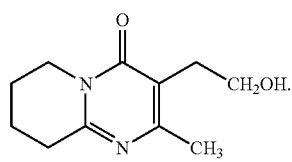

8. A process according to claim 7, wherein the oxidation is carried out by procedures based in the use of dimethyl sulfoxide in the presence of an electrophilic agent selected from the group consisting of oxalyl chloride, dicyclohexylcarbodiimide, acetic anhydride, trifluoroacetic anhydride and sulphur trioxide.

9. A process according to claim 8, wherein the reaction is performed by employing oxalyl chloride as electrophilic agent accompanied by triethylamine using methylene chloride as reacting solvent.

* * * * *